United States Patent [19]

Schack et al.

[11] Patent Number: 4,522,756

[45] Date of Patent: Jun. 11, 1985

[54] ALKYL, AZIDO, NITRO ETHERS AND METHOD OF PREPARATION

[75] Inventors: Carl J. Schack, Chatsworth; Joseph E. Flanagan, Woodland Hills, both of Calif.

[73] Assignee: Rockwell International Corporation, El Segundo, Calif.

[21] Appl. No.: 479,423

[22] Filed: Mar. 28, 1983

[51] Int. Cl.³ .................... C07C 117/00; C07C 77/02
[52] U.S. Cl. ...................................... 260/349; 149/92; 260/467
[58] Field of Search ................................ 260/467, 349

[56] References Cited

U.S. PATENT DOCUMENTS

| | | | |
|---|---|---|---|
| 3,453,108 | 7/1969 | Delzenne et al. | 260/349 |
| 3,549,687 | 12/1970 | Bachman et al. | 260/467 |
| 3,759,977 | 9/1973 | Pessina | 260/467 |
| 3,822,235 | 7/1974 | Hunter et al. | 260/349 X |
| 3,883,377 | 5/1975 | Wright | 260/349 X |
| 4,268,450 | 5/1981 | Frankel et al. | 525/403 X |
| 4,440,687 | 4/1984 | Witucki et al. | 260/349 |

*Primary Examiner*—Joseph Paul Brust
*Attorney, Agent, or Firm*—H. Fredrick Hamann; Harry B. Field

[57] ABSTRACT

A family of compounds using as energetic plasticizers having the general structural formula $R-N(NO_2)-CH_2CH_2CH_2(OCH_2CH_2)_2X$ wherein R is an alkyl group having from 1 to 10 carbon atoms and wherein X is a $-ONO_2$ or $-N_3$ radical, and their method of preparation.

6 Claims, No Drawings

ALKYL, AZIDO, NITRO ETHERS AND METHOD OF PREPARATION

BACKGROUND OF THE INVENTION

1. Field of the Invention

This invention pertains to plasticizers for pyrotechnic materials and, more specifically, to energetic plasticizers of reduced volatility for solid propellant systems.

2. Description of the Prior Art

Solid propellants are formulated from an oxidizer and fuel together with suitable binders and plasticizers to impart physical integrity. Most highly energetic systems utilize binders and plasticizers containing energetic groups such as nitro (—$NO_2$), fluorodinitro (FC($NO_2$)$_2$—), difluoroamine (—$NF_2$), and many others.

Utilization of azido plasticizers has become a reality during the last several years. These azido plasticizers impart additional energy to propellants since each azido group present adds approximately 85 kcal/mole of energy to the system. It follows that utilization of an azido polymer would impart additional energy to the system. Unfortunately, the few azido polymers synthesized to date are not functionally terminated which is a necessity for good propellant castability and physical properties.

One functionally terminated azido polymer is taught by Delzenne et al, U.S. Pat. No. 3,453,108. Another is the hydroxy-terminated aliphatic polyether having directly pendant alkyl azide groups of U.S. Pat. No. 4,268,450. In that this plasticizer has a completely different structural formula, completely different chemical and physical properties, the teachings of the prior art would not render obvious the presently claimed alkyl, azido, nitro ethers.

SUMMARY OF THE INVENTION

Accordingly, there is provided by the present invention a family of compounds having the general chemical formula

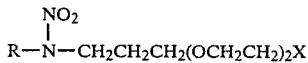

wherein R is an alkyl group having from 1 to 10 carbon atoms and wherein X is a radial selected from the group consisting of —$ONO_2$ and —$N_3$. These compounds are especially useful as energetic plasticizers of low volatility.

OBJECTS OF THE INVENTION

Therefore, it is an object of the present invention to provide energetic plasticizers of reduced volatility.

Another object of the present invention is to provide plasticizers of high molecular weight.

Yet a further object of the present invention is to provide energetic plasticizers which retain good fluid properties.

Other objects, advantages and novel features of the present invention will become apparent from the following detailed description of the invention.

DESCRIPTION OF THE PREFERRED EMBODIMENTS

In order to obtain improved energetic plasticizers of reduced volatility, a synthesis effort was carried out which sought higher molecular weight species. These materials retained good fluid properties through the incorporation of both ether and amine links in the aliphatic chain, together with the energetic nitro and azido substituents.

The family of compounds of the present invention are alkyl, azido, nitro ethers of the general formula

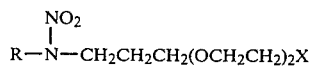

wherein R is an alkyl group having from 1 to 10 carbon atoms and wherein X is either a —$ONO_2$ or —$N_3$ radical.

In order to prepare this novel class of energetic plasticizers, n—RBr is reacted with commercially available $H_2NCH_2CH_2CH_2(OCH_2CH_2)_2OH$ to yield n—$RNHCH_2CH_2CH_2(OCH_2CH_2)_2OH$. This compound is then nitrated with $HNO_3$, acetic anhydride, and HCl to yield the RN($NO_2$)$CH_2CH_2CH_2(OCH_2CH_2)_2ONO_2$, the first of the novel energetic plasticizers. The RN($NO_2$)$CH_2CH_2CH_2(OCH_2CH_2)ONO_2$ then is taken through a displacement reaction with an azide such as sodium azide in the presence of a polar solvent such as dimethyl formamide to yield RN($NO_2$)$CH_2CH_2CH_2(OCH_2CH_2)_2N_3$.

By way of example and not limitation, the following reactions were run to produce 1-nitrato-3, 6-dioxa-10-nitrazatetradecane. The starting material for this sequence of reactions was a commercial aminoalkanol ether, $H_2NCH_2CH_2CH_2(OCH_2CH_2)_2$, designated H-163. Alkylation of one of the amine hydrogens was the first step which provided a significantly higher molecular weight product (219 va 163 g/mole) suitable for nitration.

A 0.253 mole quantity of H-163 was stirred and heated at 55°–65° C. for 4 hours. After cooling to room temperature, a solution of 25% KOH (0.7 mole) was added and the formed white precipitate filtered off resulting in a golden yellow solution which was left overnight. The addition of 125 ml of water did not result in a phase separation and the entire solution was extracted three times with 75 ml $CH_2Cl_2$. This extract was washed three times with 75 ml $H_2O$, the bulk of the $CH_2Cl_2$ was removed with gaseous nitrogen, and a final concentration effected by rotary evaporation. There was obtained 57.9 g of a dark yellow liquid corresponding to a 70.3% yield based on the equation shown

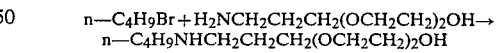

Indicative of the desired conversion was the observation that the prominent $NH_2$ deformation band of the H-163 starting material was absent in the product while strong NH and OH stretching modes remained. Elemental analyses, C, H, and N, for the alkylated derivative were satisfactory confirming the identification.

Nitration of the NH and OH functions of this compound, designated BuH-163, was accomplished using anhydrous nitric acid. Thus, 0.27 mole $HNO_3$ in 20 ml $CH_2Cl_2$ was cooled at 2°–5° C. and 0.116 mole BuH-163 in 20 ml $CH_2Cl_2$ was added during 1.75 hours before warming to ambient temperature. Acetic anhydride, 0.35 mole, and 0.5 ml of 37% HCl were added at 35° C. over 1 hour followed by an additional 30 minutes stirring. The reaction was quenched by dumping onto 100 g of ice and this solution was left overnight. Layer separation occurred and the $CH_2Cl_2$ layer was removed. The water layer was extracted with 30 ml $CH_2Cl_2$ and the combined organic layers washed four times with 35 ml saturated with $Na_2CO_3$. After removal of the $CH_2Cl_2$ with gaseous nitrogen, rotary evaporation at 30°–35° C. for 2 hours resulted in the dark red product, 26.3 g, a 73.5% yield based on the equation below.

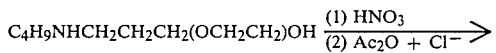

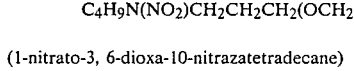

(1-nitrato-3, 6-dioxa-10-nitrazatetradecane)

An infrared spectrum of this liquid showed no appreciable NH and OH stretching bands as expected while strong $NO_2$ bands near 1650 cm$^{-1}$ were present.

Displacement of the nitrato group by the azide function was the final step carried out. A 0.022 mole sample of nitrato derivative, designated BuH-163($NO_2$)$_2$ was dissolved in 10 ml DMF and heated for 22 hours at 90° C. with excess $NaN_3$, 0.035 mole. After recooling to room temperature, the DMF was removed on the rotary evaporator until the residue was oily. Three 25 ml portions of $CH_2Cl_2$ were used to extract the oil together with filtration to remove solids. Stripping of the $CH_2Cl_2$ resulted in a dark red-brown liquid, 5.6 g, an 86.9% yield based on the conversion shown.

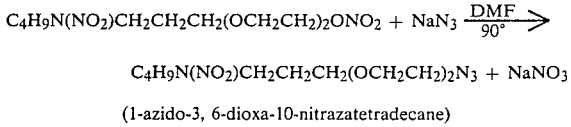

(1-azido-3, 6-dioxa-10-nitrazatetradecane)

The infrared spectrum of this liquid showed a very prominent azide stretching mode at approximately 2120 cm$^{-1}$ and a much less intense $NO_2$ band at 1650 cm$^{-1}$.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A family of compounds having the general chemical formula

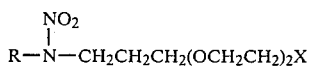

wherein R is an alkyl group having from 1 to 10 carbon atoms and wherein X is selected from the group consisting of —$ONO_2$ and —$N_3$.

2. The compound of claim 1 wherein R is —$C_4H_9$.
3. The compound of claim 2 wherein X is —$N_3$.
4. The compound of claim 2 wherein X is —$ONO_2$.
5. The compound of claim 1 wherein X is —$N_3$.
6. The compound of claim 1 wherein X is —$ONO_2$.

* * * * *